US006530262B1

United States Patent
Esser

(10) Patent No.: US 6,530,262 B1
(45) Date of Patent: Mar. 11, 2003

(54) METHOD AND DEVICE FOR DETERMINING THE EXISTENCE OF LEAKS IN A SYSTEM WITH FLOWING FLUID

(75) Inventor: Olle Esser, Malmö (SE)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 09/720,050

(22) PCT Filed: May 3, 1999

(86) PCT No.: PCT/SE99/00730
§ 371 (c)(1),
(2), (4) Date: Dec. 19, 2000

(87) PCT Pub. No.: WO99/67615
PCT Pub. Date: Dec. 29, 1999

(30) Foreign Application Priority Data

Jun. 25, 1998 (SE) .............................. 9802259

(51) Int. Cl.[7] .................................. G01N 3/08
(52) U.S. Cl. ................................... 73/40.5 R
(58) Field of Search ................. 73/40.5 R, 40

(56) References Cited

U.S. PATENT DOCUMENTS

| 3,695,094 A | 10/1972 | Hulme ..................... 73/40.5 |
| 3,987,662 A | 10/1976 | Hara et al. ............... 73/40.5 |
| 4,306,446 A | 12/1981 | Fukuda .................... 73/40.5 |
| 4,608,857 A | * 9/1986 | Mertens et al. .......... 73/40.5 R |
| 4,727,748 A | * 3/1988 | Horigome et al. ............. 73/40 |
| 5,350,357 A | 9/1994 | Kamen et al. ................. 604/29 |
| 5,375,455 A | * 12/1994 | Maresca, Jr. et al. .... 73/40.5 R |
| 5,948,969 A | * 9/1999 | Fierro et al. ............. 73/40.5 R |
| 6,082,182 A | * 7/2000 | Fierro et al. ............. 73/40.5 R |

FOREIGN PATENT DOCUMENTS

| EP | 0 298 587 | 1/1989 |
| WO | 95-22743 | 8/1995 |
| WO | 97/11771 | 4/1997 |
| WO | 99/02206 | 1/1999 |

OTHER PUBLICATIONS

US 3,702,074, 11/1972, Mullen (withdrawn)

* cited by examiner

Primary Examiner—Hezron Williams
Assistant Examiner—C D Garber
(74) Attorney, Agent, or Firm—Lerner, David, Littenberg, Krumholz & Mentlik, LLP

(57) ABSTRACT

A method and apparatus are disclosed for calibrating a sensor for flowing fluid in a system including a dialysis monitor, a fluid inlet and a fluid outlet, the method including applying a first pressure to the flowing fluid and detecting a first flow of the flowing fluid at the fluid input and the fluid output, applying a second pressure to the flowing fluid and detecting a second flow of the flowing fluid at the fluid input and the fluid output, and determining whether any detected differences between the first and second flows are the result of leakage in the system or are caused by the sensor.

12 Claims, 3 Drawing Sheets

METHOD AND DEVICE FOR DETERMINING THE EXISTENCE OF LEAKS IN A SYSTEM WITH FLOWING FLUID

BACKGROUND OF THE INVENTION

The present invention relates to a method for determining the presence of leaks in a system with flowing fluid and an apparatus for the same.

It is known with regard to systems with flowing fluid to determine the flow rate and/or flow velocity into the system at the input and out of the system at the output in order to control the flow of the fluid through the system with these determined values.

For example, in dialysis devices, among other things, the flow velocity of the dialysis fluid is detected both before the dialyser and after the dialyser in order to control the flow of the dialysis fluid through the dialyser, and therefore the dialysis itself.

Accordingly, it is known from International Application No. WO 95/22743 to arrange a first sensing means comprising a throttle, a pump and a pressure sensor both before and after the dialyser in the dialysis fluid conduit, the pressure sensor thereby measuring the pressure between the throttle and the pump. Thus, on the one hand as a result of the relationship between pressure and flow velocity at the throttle, a constant rate of flow can be set by maintaining a constant pressure with the pump. On the other hand, the flow velocity before and after the dialyser can be calculated with the aid of the measured pressure values, and compared.

In addition, second sensing means are arranged between the pump and the dialyser for precisely measuring the flow velocity both before and after the dialyser. In this way the ultrafiltration may be exactly defined by comparing the measured values, the difference between the values thus providing the rate of ultrafiltration.

In order to permit exact and reliable control of the dialyser fluid through the dialyser, as well as precise ultrafiltration, the sensing means before and after the dialyser must be calibrated against one another.

This is usually carried out with a constant dialysis fluid rate through the dialyser apparatus with the dialyser disconnected, the sensing means thereby being calibrated against one another such that they indicate the same value. For example, the dialysis treatment, which generally lasts about four hours, is interrupted briefly every thirty minutes for such calibration.

When a leak is present, either dialysis fluid will escape or air will enter from outside. In this case the sensing means before and after the dialyser detect or measure different values, respectively, it being impossible to determine whether these different values result from leaks or from variations within the sensing means themselves.

Thus, when a leak is present, if the sensing means are calibrated against one another such that they indicate the same value, although they actually detect or measure different dialysis fluid currents, this can lead to control defects.

This is dangerous, particularly for dialysis machines where it is important that the fluid currents supplied to and discharged from the dialyser are precisely tared. As a result of deposits, specifically on the sensing means that are connected downstream of the dialyser and in contact with the contaminated fluid in the dialyser, the detection becomes more and more imprecise with increasing operational time. For example, proteins, urea, cholesterols and the like, which have been removed from the blood in the dialyser, can be deposited at that point. Consequently the sensing means are calibrated against one another in a regularly repeated taring phase, for which the first sensing means connected upstream of the dialyser deliver(s) the reference levels. The first sensing means are in contact only with fresh dialysis fluid so that deposits, for example of the above-mentioned substances, and the resulting increasing imprecision in operation, are improbable.

The above-mentioned fat and protein deposits occurring essentially at the downstream sensing means can be dissolved and flushed out with highly alkaline sodium carbonate or other suitable means so that, for cleaning purposes, sodium carbonate, for example, is advantageously passed through the dialyser apparatus at regular intervals.

However, it is also possible that, when using a dialysis fluid containing bicarbonate, as well as calcium carbonate among other components, which under certain conditions can be precipitated out of the dialysis fluid, will be deposited on both sensing means. These calcium deposits can be removed easily with an acid, such as citric acid, for example. Therefore, an acid that dissolves and flushes away these calcium deposits is likewise advantageously passed through the apparatus at regular intervals for cleaning purposes.

The precision of the dialysis process can be maintained over a long period of time by means of the calibration and the described cleaning procedure, provided that a leak does not occur. If, for example, dialysis fluid were to escape from the system as a result of a leak, the second sensing means will indicate a lower value than that indicated by the first sensing means. This value corresponds to the actual flow, however, during taring it would be presumed that deposits were present on the second sensing means and the second sensing means would be calibrated to the higher value supplied by the first sensing means.

A consequence of this is that, for example, during ultrafiltration, a lower quantity of fluid than necessary is extracted, which can lead to severe complications for the patient.

A method for determining blood leaks in a dialyser during a high flux hemodialysis treatment is known from International Application No. WO 97/11771. If the pressure on the blood side sinks during the treatment below the pressure on the dialysate side, the dialysate flow is halted and the rate of ultrafiltration is increased so that the pressure on the blood side becomes positive relative to the pressure on the dialysate side. In this way, in the event of a leak, blood arrives on the dialysate side, and upon recommencing the dialysis flow is conducted to a blood leak detector. In this manner it is possible to detect blood leaks in the membrane of the dialyser, however other leaks in the dialyser or in the conduits leading to the dialyser cannot be determined with this apparatus.

U.S. Pat. No. 5,350,357 describes an apparatus for peritoneal dialysis with a pump apparatus for pumping the dialysate, the pump apparatus comprising a diaphragm. This is operated with fluid pressure or pressurised air, as are valves for controlling the dialysate flow. In order to determine whether the pump apparatus or the valves have leaks a positive and negative air pressure is alternately applied in a test phase. If the applied pressure falls or rises during a predetermined time period above or below a predetermined value, an error indication is generated. This allows the pump apparatus, and the control valves, to be checked for leaks. However, it cannot be determined e.g. if the dialysis conduits have a leak.

It is known from European Patent No. 298,587 to arrange two flow meters both in the dialysate conduit before the dialyser and in the dialysate conduit after the dialyser. These are calibrated against one another in a calibration phase so that each pair indicates the same value. If these values should then deviate from one another during operation an alarm is generated. However, it is not ascertainable whether the deviations result from a leak, from errors in the flow meters, or from deposits on the measurement elements of the flow meters.

In view of this background an object of the present invention according to a first aspect is to provide a method and an apparatus with which leaks can be determined in a system with flowing fluid.

According to a second aspect it is another object of the present invention to provide a method and an apparatus with which it can be determined whether a leak exists or whether deposits are present on the sensing means, in order to ensure an exact calibration of the sensing means, particularly for dialysis apparatus.

SUMMARY OF THE INVENTION

In accordance with the present invention, these and other objects have now been realized by the invention of a method for calibrating a sensor for flowing fluid in a system including a dialysis monitor, a fluid input, and a fluid output, the method comprising applying a first pressure to the flowing fluid and detecting a first flow of the flowing fluid at the fluid input and the fluid output, applying a second pressure to the flowing fluid and detecting a second flow of the flowing fluid at the fluid input and the fluid output, and determining whether any detected differences between the first and second flows are the result of leakage in the system are caused by the sensor. In a preferred embodiment, the method includes determining a first difference between the first flow of the flowing fluid at the fluid input and the second flow of the flowing fluid at the fluid input, determining a second difference between the first flow of the flowing fluid at the fluid output and the second flow of the flowing fluid at the fluid output, determining a third difference between the first difference and the second difference, determining a fourth difference between the first flow of the flowing fluid at the fluid input and the first flow of the flowing fluid at the fluid output, and determining a fifth difference between the second flow of the flowing fluid at the fluid input and the second flow of the flowing fluid at the fluid output. Preferably, the method includes determining whether the third difference is not zero, whereby the determined difference is caused by leakage in the system. In another preferred embodiment, the method includes determining whether the third difference is zero, and the fourth difference or the fifth difference is not zero, whereby the determined difference is caused by the sensor.

In accordance with one embodiment of the method of the present invention, applying of the first pressure to the flowing fluid is carried out at a first constant fluid flow rate and applying of the second pressure to the flowing fluid is carried out at a second constant fluid flow rate. In a preferred embodiment, the first and second constant fluid flow rates are the same.

In accordance with another embodiment of the method of the present invention, both the first pressure and the second pressure are either a positive pressure or a negative pressure.

In accordance with another embodiment of the method of the present invention, one of the first pressure and the second pressure comprises a positive pressure and the other of the first pressure and the second pressure comprises a negative pressure.

In accordance with another embodiment of the method of the present invention, the flowing fluid comprises a dialysis fluid.

In accordance with the present invention, apparatus has also been discovered for calibrating a sensor for flowing fluid in a system including a dialysis monitor, a fluid inlet, and a fluid outlet, the apparatus comprising at least one first detecting means for detecting a first flow of the flowing fluid at the fluid input, at least one second detecting means for detecting a second flow of the flowing fluid at the fluid output, pressure means for applying a first pressure to the system in a first phase and a second pressure to the system in a second phase, each of the first and second pressures comprising either a positive pressure or a negative pressure, and the first and second pressures being different pressures, and evaluation means for evaluating the first and second flows. In a preferred embodiment, the evaluation means includes means for providing a first difference between the first flow of the flowing fluid at the fluid input and the second flow of the flowing fluid at the fluid output, a second difference between the first flow of the flowing fluid at the fluid output and the second flow of the flowing fluid at the fluid output, a third difference between the first difference and the second difference, a fourth difference between the first flow of the flowing fluid at the fluid input and the first flow of the flowing fluid at the fluid output, and a fifth difference between the second flow of the flowing fluid at the fluid input and the second flow of the flowing fluid at the fluid output, and determining means for determining whether the differences are the result of leakage in the system or are caused by the sensor. In a preferred embodiment, the determining means determines that the determined difference is caused by a leak when the third difference is not zero. In another embodiment, the determining means determines that the determined difference is caused by the sensor when the third difference is zero and the fourth and fifth differences are not zero.

In accordance with one embodiment of the apparatus of the present invention, the evaluation means comprises a throttle, a pump, and a pressure sensor whereby a pressure can be applied to the flowing fluid thereby.

One embodiment of the present invention is achieved in a method, wherein in a first phase a first pressure is applied to the fluid and the rate of flow and/or flow velocity is detected at least at the input into the system and at the output out of the system, in a second phase a second pressure that differs from the first pressure is applied to the fluid and the flow rate and/or flow velocity is detected at least at the input into the system and at the output out of the system, and an indicator is formed from the detected values which indicates a leak in the system.

In this way it is possible to recognise a leak in a system with flowing fluid in a simple manner, because two different pressures are applied successively to the fluid in only one check phase, and the values detected in this way by the sensing means indicate a leak. If the values determined in the first phase and in the second phase at the input and output deviate from one another, then a leak is present.

The term "leak" is intended to signify every kind of leak that can arise in a system with flowing fluid. For example, this can concern leaks that are in valves present in the system and allow fluid to move undesirably from one system area to the next one, but do not allow fluid to escape from or enter the system. Systematic leaks which arise particularly in systems with rigid walls when the latter have holes or tears and permit fluid to flow into or out of the system can likewise be concerned. However, non-uniform leaks which arise specifically in systems with elastic walls when the latter have tears or the like can also be concerned. In that case the tears can close at one pressure owing to the given elasticity of the walls while opening at another pressure, so that discontinuous leaks result.

Preferably a first difference is formed between the values determined in the first phase and in the second phase at the input, a second difference between the values determined in the first phase and the second phase at the output, and a third difference between the first and second differences. The third difference is the indicator for a leak in the system, a leak having occurred when the third difference is not equal to zero.

In this way it can be ascertained in a simple manner using a single value, whether a leak is present in the system, so that appropriate measures may be subsequently taken to deal with the leak.

Another object of the present invention is achieved in a method wherein,
  a fourth difference is determined between the values determined at the input and the output in the first phase,
  a fifth difference is determined between the values determined at the input and the output in the second phase, and
  a discriminator indicates whether the deviations of the detected values are the result of a leak or are caused by the sensing means. In this regard the deviations are due to the sensing means when the third difference equals zero and the fourth or fifth difference is not equal to zero.

In this manner it can be ascertained whether the values determined in both phases can, for example, be used for calibration of the sensing means against one another so that an exact calibration can be ensured.

If a fluid flow of, for example, 500 ml/min is passed through the system, 20 ml/min of fluid will for example exit at the location of a leak upon applying a first predetermined positive pressure, so that at the output of the system only 480 ml/min will be determined. If in the second phase a higher second pressure is applied to the flowing fluid, an increased quantity of fluid will exit, for example 40 ml/min. Thus, at the output a fluid quantity of only 460 ml/min will be measured coming out of the system when 500 ml/min of fluid is again passed through the system. In this example the difference at the input amounts to 0 ml/min, while it amounts to −20 ml/min at the output. The third difference between these two values likewise amounts to −20 ml/min and therefore indicates that a leak is present in the system. If the deviating value determined at the output in the first phase were the result of an error in the sensing means and not of a leak in the system this deviating value would also occur upon applying the higher pressure in the second phase. In this case the difference at the output of the system would then be equal to zero, so that the third difference would be equal to zero and would indicate that no leak is present. In this case it would only be necessary to calibrate the sensing means at the input and the output of the system against one another, as the values at the output deviate from those determined at the input in both the first and second phases.

It is not necessary that the fluid flow which is passed through the system in the first phase be equal to the fluid flow passed through the system in the second phase, even though this is provided to simplify the investigation of leaks according to a preferred embodiment hereof. It is only necessary that the fluid flow passed through the system in each phase is constant so as to enable an exact prediction regarding the presence of leaks in the system to be made. For example, if a fluid flow of 500 ml/min is passed through the system in a first phase and a value of 480 ml/min is indicated at the output of the system as a result of an error in the sensing means, a value of 460 ml/min will be indicated at the output in the second phase when a fluid flow of 480 ml/min is passed through the system. In this case the differences at the input into the system and at the output out of the system amount to −20 ml/min in both phases, so that the third difference derived from these is equal to zero. This indicates that the deviations are due to errors in the sensing means and not to leaks in the system, since the third difference is equal to zero and the fourth and fifth differences are not equal to zero.

It should be mentioned at this point that the so-called output of the system may comprise several individual outputs, and likewise, the so-called input may comprise several individual inputs. In such a case, the values detected at the individual outputs or the individual inputs, respectively, would be combined in each respective phase to a single output or input value, respectively, which would then be used to form the differences in the described fashion. However, for the sake of simplification only a single input or output will be referred to in the following, although several inputs or outputs, respectively, which together form the respective input or output of the system, are always also included therein.

If a leak is present which, in a first phase, allows 20 ml/min of fluid to exit with a predetermined first pressure and a fluid flow of 500 ml/min, 480 ml/min will be detected at the output of the system. This leak allows more fluid to exit in a second phase with a higher predetermined pressure. Thus, if only 480 ml/min of fluid is passed through the system in the second phase 30 ml/min of fluid, for example, will exit, and at the output of the system only 450 ml/min will be detected. Thus the difference at the input amounts to −20 ml/min, at the output to −30 ml/min and the third difference between these two amounts to −10 ml/min. Thus it is clearly indicated that a leak is present in the system.

There can also be a situation wherein the difference ascertained at the output is zero despite the presence of a leak in the system. For example, if a fluid flow of 480 ml/min is passed through the system in the first phase, and 20 ml/min of fluid exits through a leak at a first predetermined pressure, more than 20 ml/min of fluid will exit there at a second predetermined higher pressure. For a fluid flow through the system of, for example, 500 ml/min this can then lead to 40 ml/min of fluid exiting at the leak, so that a fluid rate of 460 ml/min will likewise be indicated at the output. Thus, the difference at the output is equal to zero while at the input it amounts to +20 ml/min. Consequently, the third difference derived from this is also +20 ml/min and hence, owing to its deviation from zero, clearly indicates the presence of a leak in the system.

The pressure applied to the fluid in the first phase can be a positive pressure, as can the pressure applied to the fluid in the second phase. Only the difference between the pressures in the first and second phases is essential, it being also possible when considering this requirement to apply a negative pressure to the fluid in both the first and second phases.

It is, however, also possible to apply a negative pressure in the first phase and a positive pressure in the second phase, or vice versa. If a fluid flow of, for example, 500 ml/min is passed through the system in the first phase and a positive pressure applied, fluid can flow out of a leak at a rate of 20 ml/min, for instance, so that at the output of the system only 480 ml/min is detected. If a negative pressure is now applied in the second phase with a fluid flow of 480 ml/min, fluid can enter the system through the leak so that at the output 500 ml/min could be detected, for example. With this example a first difference of −20 ml/min will be detected at the input into the system and a second difference of +20 ml/min at the output of the system so that the third difference resulting from these two differences is +40 ml/min. Here again the presence of a leak in the system is clearly indicated by the deviation from zero of the third difference.

It is, however, advantageous when a positive pressure is applied in both the first and second phases. In this way fluid will always exit from the system in the event of a leak which is advantageous, particularly for dialysis apparatus. Impurities from outside could then not penetrate into the dialysis apparatus which would be possible when applying a negative pressure in both phases due to the penetration of fluid through a leak.

One object of the present invention is realized in apparatus wherein
  at least a first and second means for detecting the flow rate and/or flow velocity of the fluid are provided, the first means being arranged at the input of the system and the second means being arranged at the output of the system,
  means for generating a negative and/or positive pressure are provided in the system, the means being formed such that a first pressure can be applied to the fluid in a first phase and a second pressure can be applied to the fluid in a second phase, the first pressure differing from the second pressure,
  and means are provided for evaluating the flow rates and/or flow velocities detected by the sensing means.

In this way a device for determining the presence of leaks in a system with flowing fluid is provided at a very low cost. Only means for sensing the flow rate and/or flow velocity, means for generating a negative and/or positive pressure and means for evaluating the values supplied by the sensing means are required. It should be noted at this point that in a system with several inputs and/or outputs, at least one sensing means is provided at every input or output, respectively. The above-described input or output can consequently comprise several inputs or outputs, respectively, and the latter condition is considered comprised in any future reference to an input or output, respectively.

Advantageously the evaluating means are formed such that they
  determine a first difference value between the values supplied by the first sensing means in the first pressure phase and in the second pressure phase,
  determine a second difference value between the values supplied by the second sensing means in the first pressure phase and the second pressure phase, and
  determine a third difference value between the first and second difference values, the third difference value being the indicator for the presence of a leak in the system, a leak being present when the third difference is not equal to zero.

In this manner the method described above can easily be applied, the third difference supplying a value, or being an indicator, by means of which it can be determined if a leak is present in the system, so that appropriate measures may subsequently be taken to deal with the leak.

Another object of the present invention is achieved in an apparatus wherein the evaluating means are formed such that they
  determine a fourth difference between the values determined at the input and the output in the first phase,
  determine a fifth difference between the values determined at the input and the output in the second phase, and
  provide a discriminator that indicates whether the deviations of the detected values result from a leak or are caused by the sensing means. In this regard the deviations are due to the sensing means when the third difference is equal to zero and the fourth or fifth difference is not equal to zero.

In this manner it can be ascertained whether the values determined in the different phases can be used for calibration of the sensing means, as described extensively above, so that an exact calibration is ensured.

Hence, with little cost, apparatus for generating a discriminator is provided which unequivocally determines whether the deviations at the sensing means are the result of a leak, or are due to soiling or other defects of the sensing means.

Advantageously, the means for detecting the fluid flow rate and/or flow velocity each comprise a throttle apparatus, pump means and a pressure sensing means, and are arranged such that pressure can be applied to the fluid. On the one hand, this permits the flow velocity to be determined in a simple manner as a result of the above-mentioned relationship between pressure and flow velocity of the fluid at the throttle. On the other hand, the pressure applied to the fluid can be controlled just as simply with the pump means. To this end the throttle apparatus and the pump means are advantageously arranged such that the pump of the sensing means disposed at the input is arranged after the throttle apparatus, and the pump of the sensing means disposed at the output is arranged before the throttle apparatus. In both cases the pressure sensing means are arranged between the respective pump means and the throttle apparatus. The pressure in the system can be regulated in a simple manner by increasing or reducing the throughput of the respective pumps.

BRIEF DESCRIPTION OF THE DRAWINGS

The present invention will be more fully appreciated with reference to the following detailed description, which, in turn, refers to the drawings, in which.

DETAILED DESCRIPTION

Figure 1:
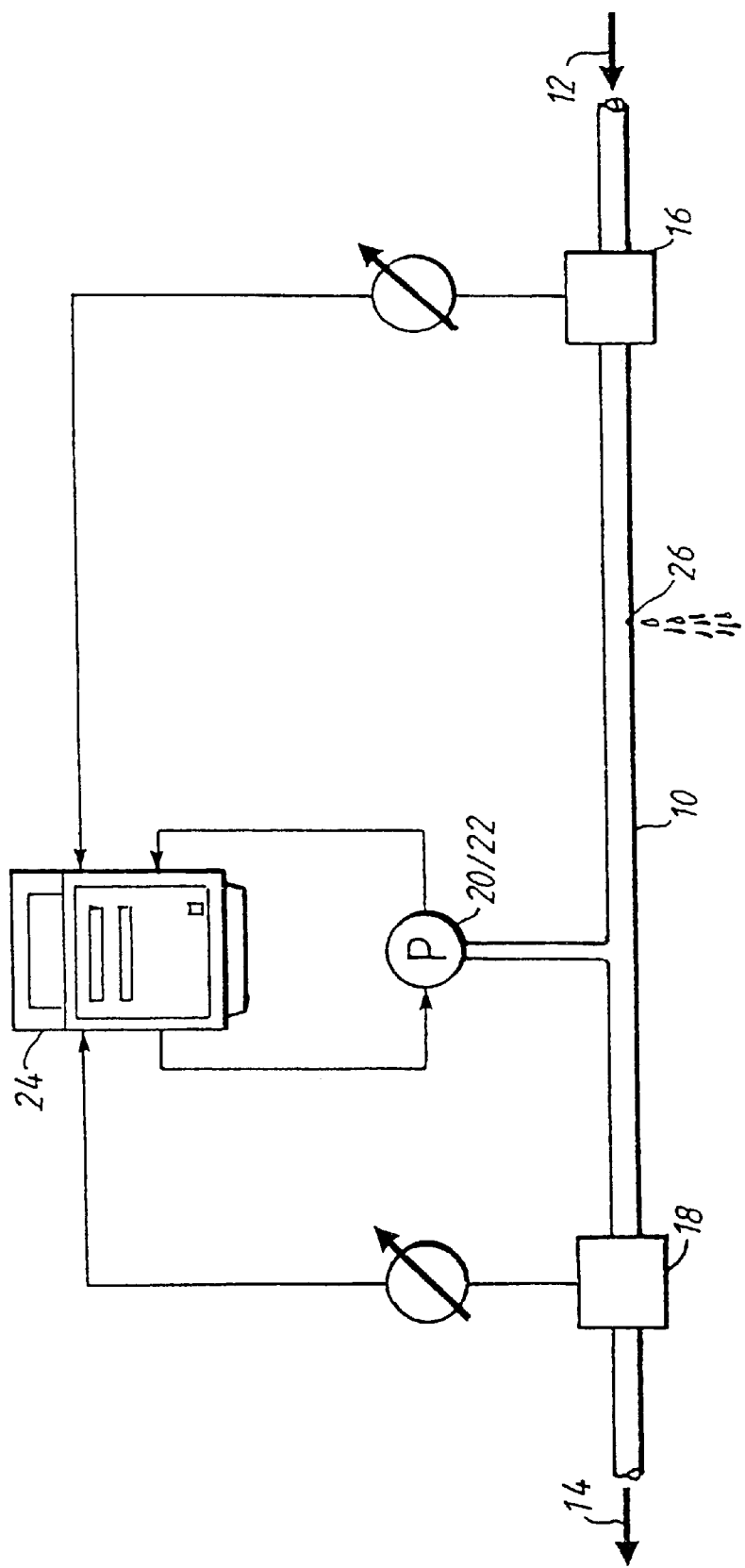
FIG. 1 is a schematic representation of a system with flowing fluid.

Referring to the Figures, in which like reference numerals refer to like elements thereof, FIG. 1 shows a system with flowing fluid which is illustrated schematically. This system is formed of a conduit 10, to which fluid is supplied and out of which fluid is emitted, as shown by the arrows 12 and 14. It should be noted at this point that the system with flowing fluid mentioned here may be part of a larger system or constitute a complete closed system in itself.

A sensing means 16 is arranged at the input into the pipe 10, as is a sensing means 18 at the output. These sensing means detect the flow velocity of the fluid passed through the conduit 10, and supply this value to evaluating means 24.

Furthermore, a pressure sensing means 22 is provided, which in this case is simultaneously formed as pressure generating means 20. This pressure sensing means also supplies the determined pressure to the evaluating means 24, while the evaluating means 24 in turn regulates the pressure generating means 20.

If the sensing means, 16 or 18, indicate different values for a constant fluid flow, this can be due to the sensing means, 16 or 18, either having deposits of particles from the flowing and possibly contaminated fluid, or being worn. However, it can also be caused by the conduit 10 having a leak 26 through which fluid exits as indicated by the dashed line at 26. In the event of the deposition of particles or wear of the sensing means, 16 or 18, the latter need simply be calibrated against one another so that they again both indicate the same value with the constant fluid flow, as disclosed in International Application No. WO 95/22743, for example.

However, if the conduit 10 has a leak 26 through which fluid exits, the sensing means, 16 or 18, detect the actual fluid flow and therefore indicate different values. If the sensing means were calibrated against one another at this point, this would lead to a fatal control error in the system.

Thus, in order to determine whether the deviations of the sensing means, 16 or 18, are due to wear or are caused by a leak 26 in the conduit 10, a test procedure for determining the presence of leaks in the conduit 10 is carried out. This test procedure supplies, inter alia, a discriminator, with the aid of which it can be ascertained whether the values determined in the test procedure can be used for calibrating the sensing means against one another. To this end, a first positive pressure, for example, is applied to the fluid in the conduit 10 in a first phase, so that a certain quantity of fluid exits from the leak 26. In this first phase a constant fluid rate of, for example, 500 ml/min is passed through the conduit 10. Then at the leak 26, 20 ml/min, for example, will exit, so that the sensing means 18 at the output of the conduit 10 will detect a fluid flow of only 480 ml/min.

Subsequently, in a second phase a second higher pressure is applied to the fluid, which here again is passed through the conduit 10 at a constant 500 ml/min. As a result of the higher pressure, a larger quantity of fluid will exit from the leak 26, for example 40 ml/min. Thus, the sensing means 18 at the output of the conduit 10 will detect only 460 ml/min. In this way the first difference between the values detected by the sensing means 16 at the input in both phases is equal to zero, while the second difference between the values detected by the sensing means 18 at the output of the conduit 10 in both phases amounts to −20 ml/min. Consequently the third difference formed from both these differences is −20 ml/min, which indicates that a leak is present in the conduit 10. If no leak were present and the deviations of the values detected by the sensing means, 16 or 18, were due to wear of the sensing means, 16 or 18, then the deviation with different pressures, and therefore also the first and second differences, would be the same, so that the third resulting difference would be equal to zero. In this case the fourth difference of the values determined at the input and output in the first phase, and the fifth difference of the values determined at the input and output in the second phase would not be equal to zero, so that the discriminator formed therefrom would indicate that the values determined in the first and second phases could be used for the calibration of the sensing means.

It should also be noted at this point that only the difference between the pressures in the two phases is important, as has been described at length above. The pressures can be either positive or negative here, or one may be positive and the other negative. When applying a negative pressure in the conduit 10, the surrounding fluid, for example air, will be sucked into the conduit 10 so that the sensing means at the output of the conduit 10 indicate a higher fluid value.

Figure 2:
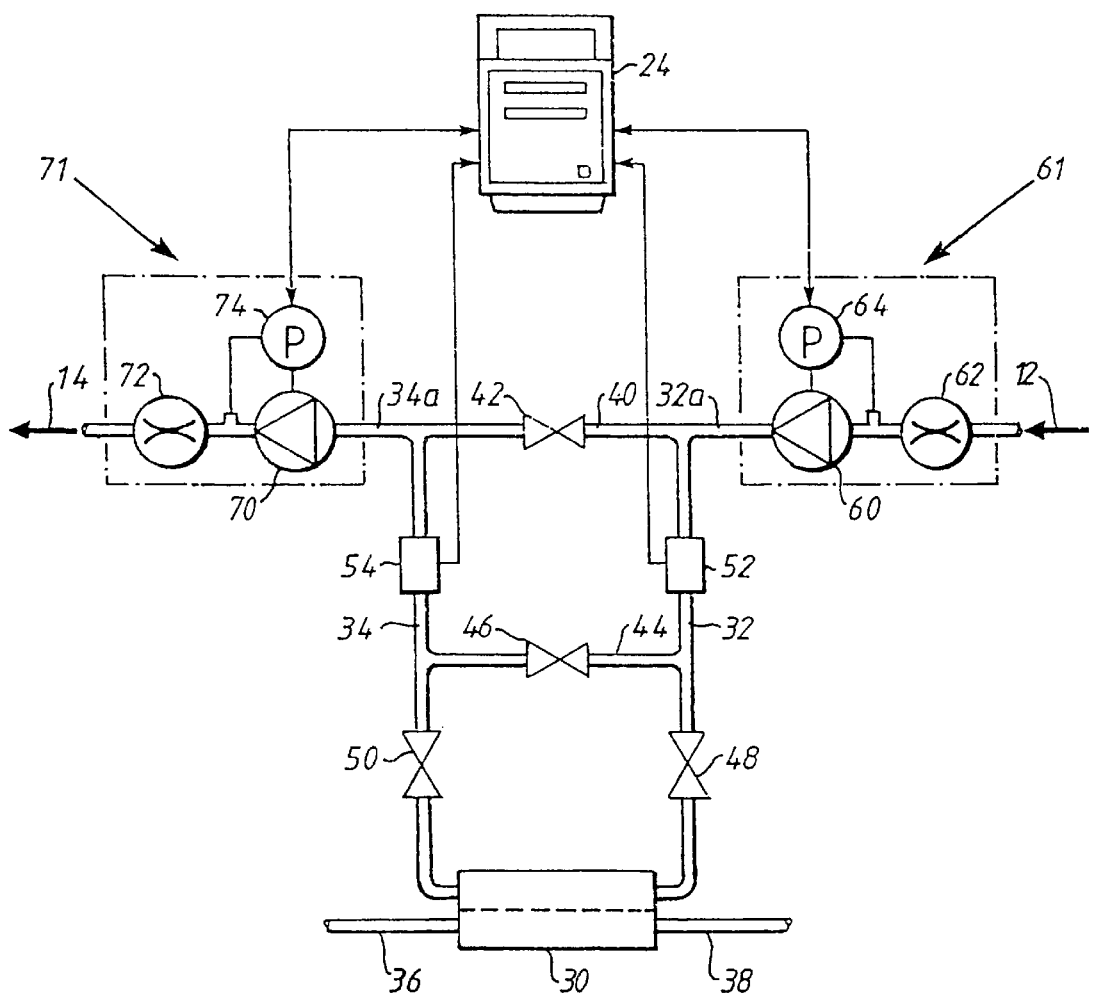
FIG. 2 is a schematic representation of part of a dialysis apparatus with a dialyser.

Part of a dialysis apparatus is shown schematically in FIG. 2. This shows the dialysate supply conduit 32 to a dialyser 30 and the dialysate discharge conduit 34 that discharges the contaminated dialysate from the dialyser 30. The dialysate supply and discharge conduits, 32 and 34, respectively, shown here form part of the whole dialysis apparatus that is not depicted in total, and in which the method for determining leaks is applied.

Sensing or control means 61, that is referred to as a restrictor in the following discussion and comprises a pump 60, a throttle 62 and a pressure sensor 64, is arranged at the input of the dialysate supply conduit 32. The dialysate supply conduit 32 is connected to the dialysate discharge conduit 34 by two bypass conduits, 40 and 44. At the output of the dialysate discharge conduit 34, which output also constitutes the output of the illustrated system, there is arranged a second sensing or control means 71, which is referred to as a restrictor in the following discussion, and comprises a pump 70, a throttle 72 and a pressure sensor 74. A bypass valve, 42 and 46, respectively, is arranged in each bypass conduit, 40 and 44, respectively. A UF cell, 52 and 54, respectively, is disposed in each of the dialysate supply conduit 32 and the dialysate discharge conduit 34 between the two bypass conduits, 40 and 44.

At this point it should be noted that the above-described sensing means can be constructed in any other desired way and can be replaced with other suitable means. For example, it may comprise gear pumps, piston pumps or other constant volume pumps which allow the exact detection and control of the dialysate flow.

A cut-off valve 48 is arranged in the dialysate supply conduit 32 between the dialyser 30 and the bypass conduit 44, and a cut-off valve 50 is arranged in the dialysate discharge conduit 34 between the dialyser 30 and the bypass conduit 44, so that the dialyser 30 can be completely isolated from the dialysate supply and discharge. This is necessary both for the taring of the sensing means and for the determination of leaks, since, for example, additional fluid can reach the dialysate circuit through the membrane of the dialyser and cause erroneous results on taring, or indicate the presence of a leak. The dialyser 30 is further connected to a patient by the blood conduits, 36 and 38, which are only suggested.

Both the UF cells, 52 and 54, and the pressure sensors, 64 and 74, are connected to an evaluating means 24. The pressure sensors, 64 and 74, detect the pressure between the throttle, 62 or 72, respectively, and the pump, 60 or 70, respectively. These determined pressure values are passed on to the evaluating means 24, which calculates the fluid flow in the dialysate supply conduit 32 or the dialysate discharge conduit 34, as previously described with respect to the relationship between flow velocity and pressure at the throttle.

The fluid flow rate through the above-described system can be calculated with the aid of both described first and second restrictors, 61 and 71, while the UF cells, 52 and 54, measure the fluid flow. This is necessary for defining the ultrafiltration rate, which is calculated from the difference between the dialysis fluid supplied to the dialyser 30 and the dialysis fluid discharged from the dialyser 30.

However, during operation of the dialysis apparatus, particles that are taken up by the dialysis fluid in the dialyser 30 are deposited both on the UF cell 54 arranged in the dialysate discharge conduit 34 and on the throttle 72 and the pump 70. Thus, with increasing operating time, the detection or measurement of the fluid flow becomes increasingly imprecise so that a calibration of the UF cells, 52 and 54, and of the first and second restrictors, 61 and 71, must occur at predetermined intervals. During this, the first restrictor 61 is tared against the second restrictor 71, and the UF cell 52 is tared against the UF cell 54. The first restrictor 61 and the UF cell 52 supply the reference values for this, as they are only in contact with fresh dialysis fluid and accordingly particles or substances from the blood are not deposited here. Deviations between these two sensing means are therefore improbable.

The method for determining leaks, which supplies the above-described discriminator, can be carried out in combination with the taring of the sensing means so that no additional procedural step is necessary. In addition, the means already present in the dialysis apparatus can be used, so that in addition no supplementary means need be installed in the dialysis apparatus.

The taring of the sensing means also occurs in two phases, as for the determination of leaks. In the first phase, the restrictor 71 at the output is calibrated against the restrictor 61 at the input, and the zero value of the UF cells, 52 and 54, is defined. To this end the bypass valve 42 in the bypass conduit 40 is opened, and the bypass valve 46 in the bypass conduit 44 and both cut-off valves, 48 and 50, are closed. Then a constant fluid current is supplied as indicated by the arrow 12 and is passed through the first section 32*a* of the dialysate supply conduit 32 to the bypass conduit 40, and further to the first section 34*a* of the dialysate discharge conduit 34, where it is discharged as indicated by the arrow 14.

The values detected by the pressure sensors, 64 and 74, during this operation are supplied to the evaluating means 24 and are used there for calculating the fluid flow rate. Since a constant fluid current is passed through the first section 32*a* of the dialysate supply conduit 32, the bypass conduit 40 and the first section 34*a* of the dialysate discharge conduit 34, the same fluid current flows through the first and second restrictor, 61 and 71, so that these should show the same value. Naturally, this presupposes that no leaks are present. If the restrictors, 61 and 71, should however show different values, these will be stored in the evaluating means 24 for a subsequent correction.

In the first phase, the measurement values supplied by the UF cells, 52 and 54, are furthermore supplied to the evaluating means 24. Both should indicate a zero value as no fluid flows through the UF cells, 52 and 54. If, however, these indicate a value, the same can be stored in the evaluating means 24 for a subsequent zero value calibration, this calibration naturally only being carried out when no leak is present.

In the first phase a first predetermined pressure is applied to the fluid, for example, a positive pressure. In the second subsequent phase a second predetermined pressure is applied, for example a higher positive pressure. The bypass valve 42 in the bypass conduit 40 is closed at this point, while the bypass valve 46 in the bypass conduit 44 is open. Both cut-off valves, 48 and 50, remain closed so that the fluid current flows through the dialysate supply conduit 32, the UF cell 52 and the bypass conduit 44 to the dialysate discharge conduit 34 and there through the UF cell 54 and the second restrictor 71.

This fluid rate is likewise constant and preferably the same as the constant fluid flow in the first phase. Therefore, the first restrictor 61 and the second restrictor 71 should again supply the same values to the evaluating means 24, as should also this time the UF cells, 52 and 54. If the UF cells, 52 and 54, indicate different values they can be calibrated against one another, provided the different values are not the result of a leak.

This can be ascertained by comparing the values determined by the first restrictor 61 in the first and second phases and forming a first difference, by comparing the values determined by the second restrictor 71 in the first and second phase and forming a second difference, and forming a third difference from these two differences. If this third difference is equal to zero, the deviations between the first and second restrictors, 61 and 71, in the first and second phases are the same, and no leak is present. In this case the values supplied by the first and second restrictors, 61 and 71, and stored in the evaluating means 24 can be used for a calibration, if this is necessary.

This is necessary when the fourth difference between the values at the input and at the output in the first phase and the fifth difference between the values at the input and the output in the second phase are not equal to zero, and the third difference is equal to zero. This is ascertained by the said discriminator. However, if the third difference is not equal to zero then a leak is present as described at length above. In this case the evaluating means 24 signal an alarm, or for security a second test for leaks may be carried out. Other measures can likewise be initiated by the evaluating means 24, such as stopping the dialysate flow, etc.

Figure 3:
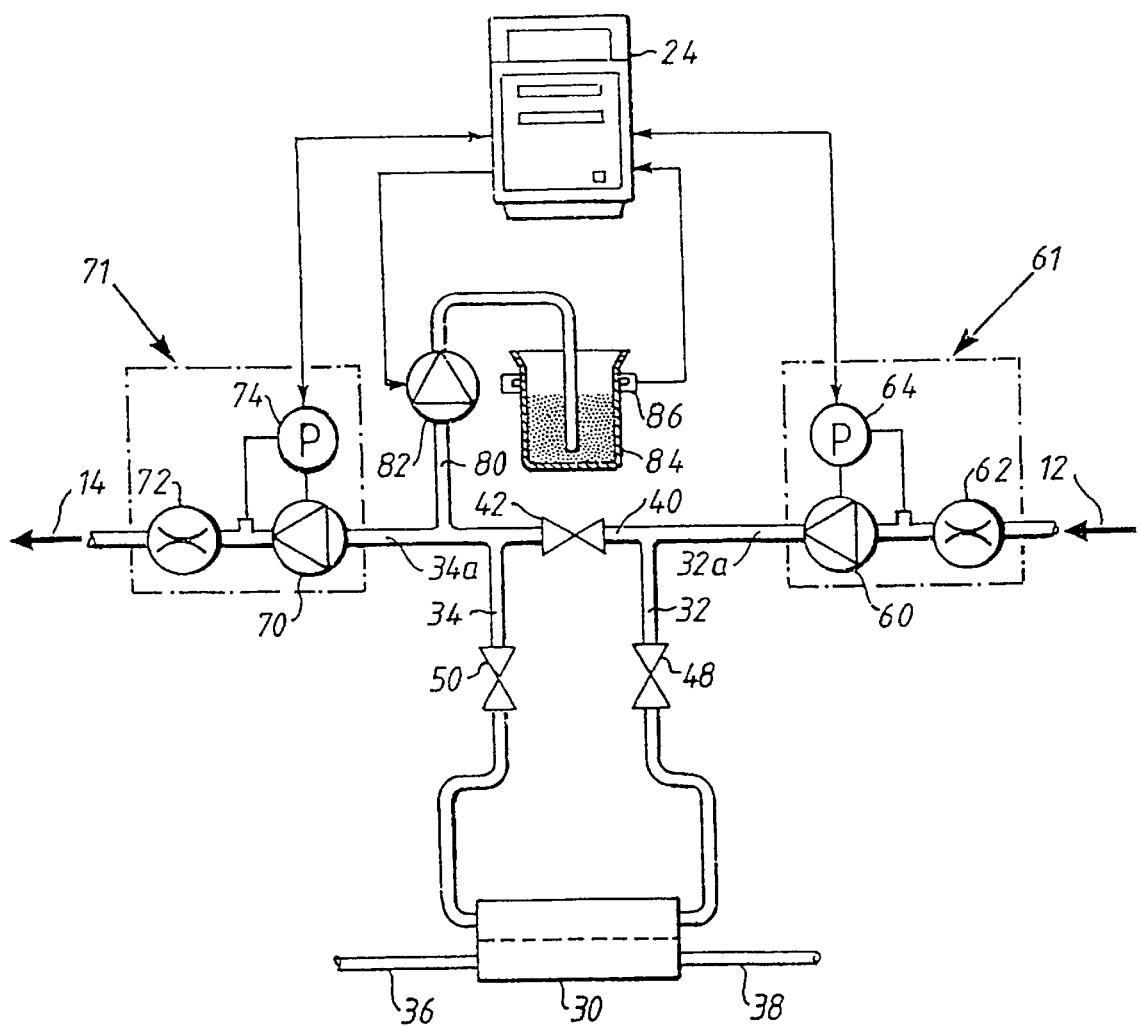
FIG. 3 is a schematic representation of part of a dialysis apparatus with a dialyser in which a second output is provided.

In FIG. 3 there is also schematically shown part of a dialysis apparatus, wherein however a second output is provided in the form of a branch conduit 80. Incidentally, like parts in this figure have been designated by like reference numerals, so that a renewed detailed description of these parts is omitted. A UF pump 82 is disposed in the branch conduit 80 and diverts a defined quantity of contaminated dialysate out of the dialysate discharge conduit 34 and into a measurement or collecting vessel 84. With this, ultrafiltration is carried out in the known manner, the extracted quantity of liquid being collected in the measurement or collecting vessel 84. The quantity of extracted contaminated dialysis fluid is measured, for example using a sensor 86 that is connected to the evaluating means 24. This in turn controls the UF pump 82 and thus, in the knowledge of the fluid rates through the restrictors, 61 and 71, respectively, regulates the rate of ultrafiltration in a known manner.

The UF pump 82 is preferably stopped during the calibration of the sensing means, 61 or 71. However, it is also possible that the UF pump 82 remain in operation during calibration, so that the value then determined at the output of the system is formed by addition in the above-described way. In the first phase, the value determined by the restrictor 71 is added to the value determined in the desired manner at the branch conduit 80, and likewise in the second phase, so that a value results that indicates the total outflow from the output of the system in each of the first and second phases. In this fashion the method described in detail above can be utilized in a simple manner for determining leaks, even for systems with several outputs, and a discriminator generated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for proving a sensor for flowing fluid in a system including a dialysis monitor, a fluid input, and a fluid output, said method comprising applying a first pressure to said flowing fluid and detecting a first flow of said flowing fluid at said fluid input and said fluid output, applying a second pressure to said flowing fluid and detecting a second flow of said flowing fluid at said fluid input and said fluid output, determining a first difference between said first flow of said flowing fluid at said fluid input and said second flow of said flowing fluid at said fluid input, determining a second difference between said first flow of said flowing fluid at said fluid output and said second flow of said flowing fluid at said fluid output, determining a third difference between said first difference and said second difference, determining a fourth difference between said first flow of said flowing fluid at said fluid input and said first flow of said flowing fluid at said fluid output, determining a fifth difference between said second flow of said flowing fluid at said fluid input and said second flow of said flowing fluid at said fluid output, and determining whether any detected differences between said first and second flows are the result of leakage in said system or caused by said sensor.

2. The method of claim 1 including determining whether said third difference is not zero, whereby said determined difference is caused by leakage in said system.

3. The method of claim 1 including determining whether said third difference is zero, and said fourth difference or said fifth difference is not zero, whereby said determined difference is caused by said sensor.

4. The method of claim 1 wherein said applying of said first pressure to said flowing fluid is carried out at a first constant fluid flow rate and said applying of said second pressure to said flowing fluid is carried out at a second constant fluid flow rate.

5. The method of claim 4 wherein said first and second constant fluid flow rates are the same.

6. The method of claim 1 wherein both said first pressure and said second pressure are either a positive pressure or a negative pressure.

7. The method of claim 1 wherein one of said first pressure and said second pressure comprises a positive pressure and the other of said first pressure and said second pressure comprises a negative pressure.

8. The method of claim 1 wherein said flowing fluid comprises a dialysis fluid.

9. Apparatus for proving a sensor for flowing fluid in a system including a dialysis monitor, a fluid inlet, and a fluid outlet, said apparatus comprising at least one first detecting means for detecting a first flow of said flowing fluid at said fluid input, at least one second detecting means for detecting a second flow of said flowing fluid at said fluid output, pressure means for applying a first pressure to said system in a first phase and a second pressure to said system in a second phase, each of said first and second pressures comprising either a positive pressure or a negative pressure, and said first and second pressures being different pressures, and evaluation means for evaluating said first and second flows, wherein said evaluation means includes means for providing a first difference between said first flow of said flowing fluid at said fluid input and said second flow of said flowing fluid at said fluid output, a second difference between said first flow of said flowing fluid at said fluid output and said second flow of said flowing fluid at said fluid output, a third difference between said first difference and said second difference, a fourth difference between said first flow of said flowing fluid at said fluid input and said first flow of said flowing fluid at said fluid output, and a fifth difference between said second flow of said flowing fluid at said fluid input and said second flow of said flowing fluid at said fluid output, and determining means for determining whether said differences are the result of leakage in said system or are caused by said sensor.

10. The apparatus of claim 9 wherein said determining means determines that said determined difference is caused by a leak when said third difference is not zero.

11. The apparatus of claim 10 wherein said determining means determines that said determined difference is caused by said sensor when said third difference is zero and said fourth and fifth differences are not zero.

12. The apparatus of claim 9 wherein said evaluation means comprises a throttle, a pump, and a pressure sensor whereby a pressure can be applied to said flowing fluid thereby.

* * * * *